United States Patent [19]

Duthinh

[11] Patent Number: 5,547,671
[45] Date of Patent: Aug. 20, 1996

[54] ANTI-INTOXICATION COMPOSITION

[76] Inventor: Phu Duthinh, 650 Huntington Ave., Boston, Mass. 02115

[21] Appl. No.: 531,351

[22] Filed: Sep. 20, 1995

[51] Int. Cl.$^6$ .......................... A61K 35/78; A61K 9/48; A61K 9/20; A61K 9/14

[52] U.S. Cl. ...................... 424/195.1; 424/451; 424/464; 424/484

[58] Field of Search .................. 424/195.1, 464, 424/451, 484; 514/811

[56] References Cited

U.S. PATENT DOCUMENTS 5,204,369  4/1993  Vallee et al. ........................ 514/456
5,324,516  6/1994  Pek ...................................... 424/195.1

OTHER PUBLICATIONS

Proc. Natl. Acad. Sci. USA, vol. 90, pp. 10008–10012, Nov. 1993, Biochemistry.

*Primary Examiner*—John W. Rollins
*Attorney, Agent, or Firm*—Karl Hormann

[57] ABSTRACT

An anti-intoxication compound for combatting the side-effects of an excessive consumption of alcohol may be taken orally as a food supplement before or after drinking, and comprises a plurality of herbal or vegetable extracts in defined quantities, at least one of them containing naturally occurring daidzin and daidzein in sufficient quantities to control the gastric and hepatic metabolism of alcohol.

5 Claims, No Drawings

ANTI-INTOXICATION COMPOSITION

BACKGROUND OF THE INVENTION

1. Field of the Invention

The present invention relates generally to an anti-intoxication preparation and, more particularly, to a compound position made of herbal extracts to be taken orally to overcome the unpleasantness inherent in excessive consumption of ethyl alcohol.

2. Brief Statement of the Prior Art

Certain herbal substances have been known in oriental countries, in particular China, for their beneficent properties in overcoming, or at least easing, the unpleasant side-effects resulting from excessive consumption of ethyl alcohol, $C_2H_5OH$. Foremost among them is a substance prepared from radix as well as *flos puerariae*, i.e., respectively, the root and the blossom of *pueraria lobota*, commonly known as kudzu, a leguminous vine. Indeed, documentation of its use in alcohol-related illness has been found as early as about 600 A.D. in the Chinese pharmacopoeia *Beiji-Qianjin-Yaofang*.

U.S. Pat. No. 5,324,516 discloses a Galenic composition said to increase, in vivo, the metabolic activity of alcohol dehydrogenase and aldehyde dehydrogenase enzymes and a pharmaceutically acceptable carrier, adjuvant or excipient therefor, including an extract of the pueraria flower, phaseoli radiati semen, pinelliae tuber and fructose in certain proportional ranges.

Keung and Vallee, in an article in Proc. Natl. Acad. Sci. USA, Vol. 90, pp. 10008–10012, November 1993, Biochemistry, have reported experiments they conducted with Syrian Golden hamsters, ascribing alcohol-suppressant effects of such herbal compositions to daidzin and daidzein, respectively a glycosylated isoflavone and a aglycone thereof. But they do not know whether these substances per se are the pharmacologically active molecules which directly suppress ethanol intake or whether they act as prodrugs converted in vivo to pharmacologically active species.

To date, none of the information available on the effects of kudzu vine extracts on alcohol consumption indicates any great success in combatting a significant social disease.

OBJECTS OF THE INVENTION

It is, therefore, an object of the present invention to provide an herbal composition including an extract of the kudzu vine which can be used as a food supplement to overcome the effects of alcoholic intoxication in humans.

Another object is to provide a composition of the general kind which can easily be made from vegetable sources.

A still further object of the invention is to provide a composition based on vegetable or herbal extracts which act on gastric and hepatic metabolisms and which provides quick physical recuperation after excessive alcohol consumption.

Other objects will in part be obvious and will impart appear hereinafter.

SUMMARY OF THE INVENTION

These and other objects will be accomplished by a currently preferred composition including, without being thus limited, an extract of the kudzu vine blossom, starch extracted from the kudzu vine root, an extract prepared from American ginseng, an extract of ginger root, extracts of tangerine and green lemon peel, an extract of magnolia tree bark, and thiamine, in proportions hereinafter set forth.

The novel features which are considered to be characteristic of the invention are set forth with particularity in the appended claims. The invention itself, however, in respect of its composition and manufacturing techniques, together with other objects and advantages thereof, will be best understood from the following description of preferred embodiments.

DETAILED DESCRIPTION OF THE INVENTION

The moderate consumption of alcohol, in private or in public, appears generally to have been accepted or condoned as an integral element of civilized and cultured human activities. Indeed, "drinking" in responsible quantities is seen as contributing to the well-being of individuals and to conviviality, at least until post festum. Ethyl alcohol is one of a few intoxicating drugs widely and legitimately available for consumption by humans generally anywhere. It is offered in a dazzling variety of distilled liquors and brewed or fermented beverages, ranging in strength from 4 to more than 75 volume-% of alcohol.

While its consumption may be tolerated and condoned, the drinking of ethyl alcohol can lead to serious physical, mental and social illnesses, cirrhosis of the liver being an example of the former and disrupted families and drunken driving examples of the latter kind. Attempts to combat the consumption of alcohol have not been lacking, the most serious and concerted, albeit unsuccessful one, being that increment of American history known as Prohibition.

For an understanding of the invention, a detailed description of the metabolism of alcohol is not thought to be necessary. Generally, however, alcohol metabolizes in vivo in two stages: First, in the alcohol dehydrogenase (ADH) converting the alcohol into acetaldehyde and, second, in the aldehyde dehydrogenase (ALDH) converting the $CH_3CHO$ into acetate. They occur gastrally as well as hepatically, with the liver supplying the co-enzyme NAD+ required in the process. In the stomach, the acetate is broken down into water and carbon dioxide, both of which are secreted. The liver converts the acetate, in separate metabolic pathways, into energy by way of the citric acid cycle and into fat through the fatty acid synthesis.

The processes may be schematized as follows:

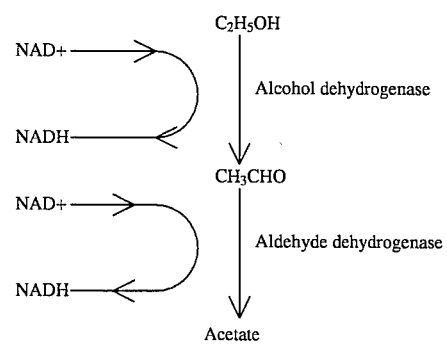

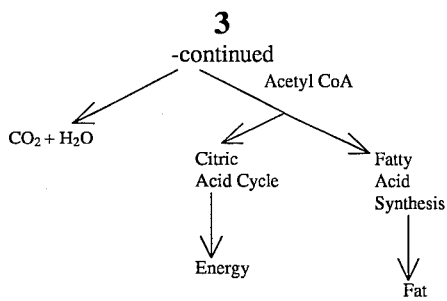

As can be seen, both gastric and hepatic metabolisms require the NAD+ (nicotine-adenine-dinucleotide) co-enzyme to break down ethanol. In the absence of this co-enzyme ethanol cannot be metabolized. In any event, the reaction of ethanol by alcohol dehydrogenase into acetaldehyde is a rate limiting reaction, and while in the presence of NAD+ large quantities of ethanol can quickly be converted into acetaldehyde, the remaining NAD+ is very likely of insufficient quantity to convert the acetaldehyde into acetate. Excess acetaldehyde will thus accumulate, enter the blood stream and the brain. Being a toxic substance, acetaldehyde will cause headaches, nausea, vomiting, diarrhea, upset stomach, dizziness, ataxia, confused consciousness—in short, all the symptoms associated with being inebriated. In acute cases, a social drinker may additionally suffer from numbness of the limbs, and in chronic cases it may progress to the Wernicke-Korsakoff syndrome, to wit, numbness of limbs, depression of the central nervous system, restlessness, ocular problems, amnesia, and coma.

Social drinkers as a rule have insufficient quantities of the enzyme and co-enzyme referred to supra. As a consequence, they become quickly inebriated and suffer from the mentioned symptoms in proportion to the amount of ethanol consumed. Since ethanol also suppresses anti-diuretic hormones (ADH), social drinkers tend to urinate excessively and become dehydrated and, consequently, thirsty. The concentration of electrolytes in their blood changes; acidosis may occur.

Alcohol addicts, however, have increased gastric and hepatic dehydrogenase and NAD+ than "social" drinkers. The constant onslaught of ethanol forces the liver to reconvert NADH to NAD+ on rather a larger scale. The result is an excessive accumulation of fatty acid, and eventually hepatic cirrhosis will set in. Alcohol also depletes thiamine (vitamin $B_1$).

It has been recognized by the present inventor that the problems associated with the consumption of alcohol can be alleviated generally by diverting some of the conversion of acetate from the liver to the stomach and, more particularly, by additionally supporting this gastral process by providing ingestible substances reducing the rate of alcohol conversion into acetaldehyde. Therefore, in accordance with the invention, ethanol is to be retained in the stomach for as long a period as possible so that it can be converted into $CO_2$ and $H_2O$ by gastric metabolism. Ideally, and to avoid the build-up of acetaldehyde, the conversion ratio of ethanol into acetaldehyde and of acetaldehyde into acetate should be 1:1. While the controlled breakdown of alcohol within the system of the body is an important element in its recuperation, it has been found that an adequate simultaneous supply of nourishment is of equal importance and must not, therefore, be neglected.

These objects are accomplished by food intake to reduce the gastric discharge and, additionally, by an agent inhibiting the alcohol dehydrogenase to slow the reaction of ethanol into acetaldehyde. Daidzin and daidzein are such agents occurring in nature in a source which is fairly common, the kudzu plant. As alcohol acts as an irritant on the gastric mucosa, an agent to protect the mucosa should preferably also be administered. Finally, to substitute for, or complement, the energy typically lost by drinking persons, certain herbs should be provided as well.

It has surprisingly been found that these requirements can be met by a composition containing the following ingredients:

1) an extract of kudzu blossom (*flos puerariae*) as a source of daidzin and daidzein to inhibit alcohol and acetaldehyde dehydrogenase;

2) starch derived from the kudzu root (*radix puerariae*) as nourishment and coating for the gastric mucosa *);

*) An additional beneficent effect is believed to derive from the fact that this starch, too, contains small quantities of daidzin and daidzein 3) extract of American ginseng (*panax quinquafolium*) as a source of quick energy (tonic);

4) an extract of ginger root (*radix zingiberis officinalis*) against vomiting;

5) extracts of tangerines peel and green lemon peel in equal proportions against stomach upset;

6) extract of magnolia tree bark against stomach upset; and 7) thiamine (vitamin $B_1$) against numbness.

The above ingredients, all of which are either commercially in Oriental natural food shops and pharmacies or apopthecaries available, or can at any rate easily be prepared from the plants referred to by extraction processes well known to those skilled in the art as dry powders, should be thoroughly mixed in the following preferred quantities: 1)—about 0.5 to about 2.5 g; 2)—about 5 to 25 g; 3)—about 0.5 to about 2.5 g; 4)—about 0.5 to about 2.5 g; 5)—about 0.5 to about 2.5 g; and 6)—about 0.5 to about 2.5 g; and 7)—about 50 mg.

After mixing, the composition may be left in its powdery state. Preferably, however, it is pressed into tablets or lozenges weighing about 20 g each. It may be found to be advantageous to add an inert or base binder matrix material of the kind well known to persons skilled in the art to the compound to improve its compaction into tablets, without, however, interfering with the defined relative and absolute quantities of its ingredients. Alternatively, the powder may be packaged in small pouches or capsules of suitable digestible materials. Another possibility of packaging the compound would be its suspension in candy bars to accommodate the craving of inebriated persons for sugar. It may, optionally, also have flavoring agents added, provided, however, they do not render the composition acidic.

It has been found that if the composition is taken before drinking alcohol, the usual symptoms accompanying alcoholic intoxication are substantially avoided. Taken after drinking, the composition will also prevent the occurrence of the mentioned symptoms and it will inhibit or suppress, or at any rate quickly overcome the sensation colloquially known as hang-over.

It will be appreciated by those skilled in the art that the quantitative ranges set forth above in respect of the ingredients used in the compound of the present application are intended as examples only, certain ideal absolutes being believed possible but dependent upon the amount of alcohol consumed by a person and the general physical constitution of such person.

What is claimed is:

1. A composition for relieving the side effects of ethanol consumption in humans, comprising the following ingredients:

about 0.5 to about 2.5 g of extract of kudzu vine blossom (*flos puerariae*);

about 5 to about 25 g of starch derived from the root of the kudzu vine (radix puerariae);

about 0.5 to about 2.5 g of extract of American ginseng (*panax quinquafolium*);

about 0.5 to about 2.5 g of extract of ginger root (*radix zingiberis officinalis*);

about 0.25 to about 1.25 g of extract of tangerine peel;

about 0.25 to about 1.25 g of extract of green lemon peel;

about 0.5 to about 2.5 g of extract of magnolia tree bark; and about 50 mg of thiamine (vitamin $B_1$).

2. The composition of claim 1, further including a binder matrix.

3. The composition of claim 1, wherein said ingredients are packaged in tablet form.

4. The composition of claim 1, where said ingredients are packaged in capsule form.

5. The composition of claim 1, wherein said ingredients are packaged in pouches.

* * * * *